United States Patent [19]

Sakurai et al.

[11] 4,120,883
[45] Oct. 17, 1978

[54] METHOD FOR PRODUCING AN ORGANOMAGNESIUM COMPLEX

[75] Inventors: Hisaya Sakurai; Hideo Morita; Tadashi Ikegami; Katsuaki Maeda; Masayasu Furusato, all of Okayamaken, Japan

[73] Assignee: Asahi Kasei Kogyo Kabushiki Kaisha, Osaka, Japan

[21] Appl. No.: 750,303

[22] Filed: Dec. 13, 1976

[30] Foreign Application Priority Data

Dec. 22, 1975 [JP] Japan .................................. 50-151833
Apr. 12, 1976 [JP] Japan .................................. 51-40339
Apr. 14, 1976 [JP] Japan .................................. 51-41245

[51] Int. Cl.$^2$ ............................................... C07F 5/06
[52] U.S. Cl. ........................... 260/448 A; 260/448 R; 260/448 AD; 252/429 C; 252/431 R
[58] Field of Search ....... 260/448 AD, 448 R, 448 A; 252/431 R, 429 C

[56] References Cited

U.S. PATENT DOCUMENTS

| 2,899,415 | 8/1959 | Truett | 260/94.9 |
| 3,737,393 | 6/1973 | de Vries | 252/431 R |
| 3,850,897 | 11/1974 | Priola et al. | 526/183 X |

FOREIGN PATENT DOCUMENTS

| 18,235 | 1973 | Japan | 260/448 A |
| 1,003,551 | 9/1965 | United Kingdom | 260/448 AD |

OTHER PUBLICATIONS

Malpass et al., J. Organometal. Chem. 93, 1–8 (1975).

*Primary Examiner*—Helen M. S. Sneed
*Attorney, Agent, or Firm*—Burgess, Dinklage & Sprung

[57] ABSTRACT

A method for producing an organomagnesium complex which is soluble in an inert hydrocarbon medium and expressed by the general formula $Mg_\alpha Al_\beta R^1{}_p Y_q$ is provided. In this formula $\alpha, \beta, p$ and $q$ each is a number greater than zero,
$\alpha/\beta =$ about 0.5 to 20,
$2\alpha$ and $3\beta = p + q$.
$q/\beta =$ about 0.5 to 1.5,
Y is $OR^2$ or $OSiR^3R^4R^5$,
$R^1$, $R^2$ and $R^3$ each independently is a hydrocarbon radical having 1 to 20 carbon atoms, and
$R^4$ and $R^5$ each independently is a hydrocarbon radical having 1 to 20 carbon atoms, hydrogen or a halogen atom.

Said complex is prepared by reacting (A) an organomagnesium compound $R^1{}_aM_gX_{2-a}$ wherein x is halogen, with (B) an aluminum compound $AlYX_2$ wherein Y and X have the same meanings as above-defined. This method is superior to the prior art with respect to ease of reaction, high reaction efficiency and safety. Further the complex is safe during storage and handling. When the complex is employed as an olefin polymerization catalyst, the catalyst efficiency is higher and the characteristic properties of the resultant polymer are superior to those of polymers with other complexes.

10 Claims, No Drawings

METHOD FOR PRODUCING AN ORGANOMAGNESIUM COMPLEX

DESCRIPTION OF THE INVENTION

The present invention relates to a novel method for producing an organomagnesium complex.

Organomagnesium compounds obtained by reacting an organic halide with metallic magnesium have been known as so-called Grignard's reagents and widely used as raw materials for organic syntheses or for catalysts.

Grignard's reagents have been generally prepared using polar compounds such as ethers, which, however, are undesirable for some of the uses of the reagents. Thus, methods for synthesizing the reagents in an inert hydrocarbon medium have been studied, and methods therefor with a good efficiency have been proposed (e.g. Brice Smith, Chem. & Ind. p. 1533, 1960; Zakharkin, Tetrahedron Letter, p. 631, 1962).

However, since organomagnesium compounds are hardly soluble or insoluble in an inert hydrocarbon medium and this is disadvantageous in their industrial uses, various attempts have been made to solubilize them. In one of them, solubilization is effected by forming a complex thereof with another metallic compound. K. Ziegler obtained a complex $MgR_2[AlR'_3]_2$ by synthesizing a compound $RMgCl$ or $R_2Mg$ in an ether, removing said ether therefrom and reacting same with $AlR'_3$ in hexane (Ann. 605, 93–97, 1957). Joh et al obtained a complex $MgR_2 \cdot AlR'_3$ (wherein the ratio of Mg : Al is 1 : 1) by reacting $MgR_2$ with $AlR'_3$ in toluene or heptane (J. Polymer Sci., A-1, 2503–2522 (1967)). On the other hand, B. Smith synthesized a complex from a metallic derivative of an organic compound having a hydroxyl group or an enolizable keto group (e.g. $Al(OR)_3$) and an organomagnesium compound synthesized in a hydrocarbon, and found that said complex can be substituted for organolithiums (British Pat. Nos. 1,003,551 (1965) and 955,806 (1964)). According to a tracing experiment carried out by the present inventors, this complex is soluble in a hydrocarbon medium. Further Zakharkin proposed a method for synthesizing an organometal by reacting a Grignard's reagent synthesized in a hydrocarbon medium with a metal halide (Proceeding of the Academy Science of USSR, 144, 543–545, 1962)). According to a tracing experiment carried out by the present inventors, it has been observed that when $AlCl_3$ is used for the metal halide, a complex $[MgR_2]_6 \cdot AlR_3$ is formed in the system. Recently two methods for preparing a solution of dialkylmagnesium using the abovementioned reaction system have been proposed. Namely, according to the method of Japanese Patent Publication No. 24009/1972, dialkylmagnesium is solubilized by reacting an organomagnesium compound synthesized in a hydrocarbon medium with an organoaluminum compound expressed by a general formula $AlR_mX_{3-m}$ wherein X is alkoxy or halogen atom and $m$ is 1 to 3. Texas Alkyls Co. proposed a method for preparing a complex $[MgR_2]_m[AlR_3]_n$ by using $AlR_3$ in the abovementioned system (Japanese Patent Application laid-open No. 18235/1973).

The present inventors have made strenuous studies on a method for preparing an organomagnesium complex, and as a result found a novel method for producing an organomagnesium complex useful as a raw material for the catalyst employed in the production of Ziegler's process polyolefins, and completed the present invention.

The present invention resides in:
a method for producing a hydrocarbon-soluble organomagnesium complex of the formula $$Mg_\alpha Al_\beta R^1_p Y_q$$

wherein $\alpha, \beta, p$ and $q$ each is a number greater than zero,
$\alpha/\beta$ = about 0.5 to 20,
$2\alpha$ and $3\beta = p + q$,
$q/\beta$ = about 0.5 to 1.5,
Y is $OR^2$ or $OSiR^3R^4R^5$,
$R^1$, $R^2$ and $R^3$ each independently is a hydrocarbon radical having 1 to 20 carbon atoms, and
$R^4$ and $R^5$ each independently is a hydrocarbon radical having 1 to 20 carbon atoms, hydrogen or a halogen atom,
which comprises reacting
(A) an organomagnesium compound of the formula $$R^1_a MgX_{2-a}$$

with (B) an aluminum compound of the formula
$AlYX_2$
wherein
X is a halogen atom, and
$a$ is a positive number up to 2.

The organomagnesium compound (A) identified by the general formula $R^1_a MgX_{2-a}$, which is employed in the above-mentioned reaction, is synthesized from a halogenated hydrocarbon and metallic magnesium according to a known method for preparing Grignard's reagents. Although either of ethers or inert hydrocarbons can be employed as the solvent for the synthesis, an ether not only reduces the yield of the objective organomagnesium complex, but also is not a desirable component when the organomagnesium complex is employed as a catalyst component. Accordingly in the case of the synthesis thereof in ethers, it is desired to remove ethers. Thus organomagnesium compounds synthesized in hydrocarbons are particularly preferable.

The hydrocarbon group having 1–20 carbon atoms, expressed by $R^1$ in the above-mentioned formula is an aliphatic, aromatic or alicyclic hydrocarbon group, and among these, an aliphatic group is particularly preferable. As for this group, for example, ethyl, propyl, butyl, amyl, hexyl, octyl, decyl and dodecyl are mentioned. As for the halogen atom, X Cl, Br or I can be employed, and Cl is preferable.

The aluminum compound (B) identified by the general formula $AlYX_2$ will be described. As for the aluminum compound wherein Y is $OR^2$ in the formula $AlYX_2$, i.e. $Al(OR^2)X_2$, the hydrocarbon group $R^2$ having 1–20 carbon atoms is an aliphatic, aromatic or alicyclic hydrocarbon group, and among these, an aliphatic one such as propyl, butyl, amyl, etc. is particularly preferable. As for the examples of these compounds, $Al(OC_2H_5)Cl_2$, $Al(OC_3H_7)Cl_2$, $Al(OC_4H_9)Cl_2$, $Al(OC_5H_{11})Cl_2$, $Al(OC_6H_{13})Al_2$, $Al(OC_7H_{15})Cl_2$, $Al(OC_8H_{17})Cl_2$, $Al(OC_{10}H_{21})Cl_2$, $Al(OC_{12}H_{25})Cl_2$, $Al(OC_2H_5)Br_2$, $Al(OC_3H_7)Br_2$, $Al(OC_4H_9)Br_2$, $Al(OC_6H_{13})Br_2$, $Al(OC_8H_{17})Br_2$, $Al(OC_{10}H_{21})Br_2$, $Al(OC_2H_5)I_2$, $Al(OC_3H_7)I_2$, $Al(OC_4H_9)I_2$, $Al(OC_6H_{13})I_2$, $Al(OC_8H_{17})I_2$, etc. are mentioned.

These compounds can be synthesized according to various methods, for example, by the reaction of $AlX_3$ with $Al(OR)_3$, the reaction of $AlCl_3$, metallic Al and $R^2OH$ or the reaction of $AlR^2X_2$ with $O_2 R^2OH$.

As for the aluminum compound wherein Y is $OSiR^3R^4R^5$ in formula $AlYX_2$, i.e. $Al(OSiR^3R^4R^5) X_2$, $R_3$ is an aliphatic, aromatic or alicyclic hydrocarbon group having 1–20 carbon atoms, and $R_4$ and $R_5$ each independently is an aliphatic, aromatic or alicyclic hydrocarbon group having 1–20 carbon atoms, hydrogen or a halogen atom. Compounds wherein at least one of these groups is a hydrogen atom are particularly preferable. As for the examples of these compounds, $(H_2CH_3SiO)AlCl_2$, $[H(CH_3)_2SiO]AlCl_2$, $(H.CH_3.C_2H_5.SiO)AlCl_2$, $(H.C_4H_9.C_6H_5.SiO)AlCl_2$, $(H.CH_3.C_4H_9.SiO)AlCl_2$, $(H.CH_3.nC_8H_{17}.SiO)AlCl_2$, $[(C_2H_5)_2.C_4H_9.SiO]AlCl_2$, $(H.C_2H_5.C_6H_{13}.SiO)AlCl_2$, $[(CH_3)_2.C_2H_5.SiO]AlCl_2$, $[(Cl.(CH_3)_2.SiO]AlCl_2$, $(H_2.CH_3.SiO)AlBr_2$, $[H.(CH_3)_2.SiO]AlBr_2$, $(H.CH_3.C_2H_5.SiO)AlBr_2$, $(H_2 \quad CH_3.SiO)AlI_2$, $[H.(CH_3)_2.SiO]AlI_2$, $(H.CH_3.C_2H_5.SiO)AlI_2$, etc. are mentioned.

These aluminum compounds having a siloxy group can be synthesized according to various methods, for example, by the reaction of an aluminum compound of the formula $AlR^5X_2$ with a siloxane compound having a structural unit of the formula

or by the reaction of $AlX_3$ with $NaOSiR^3R^4R^5$.

The reaction of the organomagnesium compound (A) with the aluminum compound (B) is carried out at a temperature of about 20°–200° C., preferably about 50°–150° C., for about 0.5–20 hours. As for the reaction concentration of component (A) in carrying out this reaction, a concentration range of about 0.1–2.5 mol/l may be employed, and in order to obtain a solution of an organomagnesium complex in a high concentration, it is advantageous to elevate the reaction concentration of component (A) within a range wherein no obstacle occurs in operating the reaction. Component (B) may be employed in a concentration of about 0.005–5 mol/l. The inert-hydrocarbon-medium-soluble organomagnesium complex obtained by the reaction of (A) with (B) has a composition wherein the molar ratio of Mg/Al is in the range of about 0.5–20. This composition can be optionally varied within this range by varying the amount of component (B) to be added to component (A) in the reaction system. As for the reaction medium used in carrying out the reaction of (A) with (B), aliphatic hydrocarbons such as hexane, heptane, etc., aromatic hydrocarbons such as benzene, toluene, xylene, etc. and alicyclic hydrocarbons such as cyclohexane, methylcyclohexane, etc. may be employed.

The complex synthesized according to the above-mentioned reaction is obtained in the form of a hydrocarbon solution, and presumed to be a sole complex or a mixture of plural kinds of complexes. The composition of the complex can be given by subjecting the solution to analysis, and also it is possible to determine the average composition by measuring the molecular weight. The substituent groups in the complex are distributed to aluminum and magnesium atoms, and an exchange occurs between the substituent groups. This fact is presumed from the appearance of new absorption of NMR spectra and the broadening of the absorption. The ratio of Mg to Al, $\alpha/\beta$, is important for obtaining the soluble complex, and a range of about 0.5–20, particularly about 1–10, is preferable for obtaining a stable complex.

The specific features, effectivenesses and superiority to the known art, of the present invention will be hereinafter described in detail.

The first of the specific features of the present invention consists in that the method of the present invention is superior in the points of ease of reaction, high reaction efficiency and safety as compared with known methods. The second thereof consists in that the inert hydrocarbon-soluble complex obtained according to the method of the present invention is safe in storing and handling, and further when it is employed as an olefin polymerization catalyst, superior effectivenesses are exhibited with respect to catalyst efficiency and characteristic properties of the resulting polymer.

With regard to the above-mentioned first specific feature, in the case of the known art wherein $AlCl_3$ and $Al(OR)_3$ are employed, these compounds are hardly soluble or insoluble in an inert hydrocarbon, whereas the $AlYX_2$ compounds of the present invention are readily soluble in said solvent and very easy to employ in reaction and handling. Further, the method of the present invention provides a higher yield than known methods. This is apparent from the comparison of the data of the following Table 1.

Table I

| Experiment | Component (B) | Composition of complex[1] | Yield[2] (%) |
|---|---|---|---|
| Example 1 | $Al(OnC_4H_9)Cl_2$ | $MgAl_{0.30}(n\text{-}C_4H_9)_{2.60}(On\text{-}C_4H_9)_{0.30}$ | 64 |
| Comparative Ex. 1 | $Al(On\text{-}C_4H_9)_3$ | $MgAl_{0.29}(n\text{-}C_4H_9)_{2.23}(On\text{-}C_4H_9)_{0.64}$ | 30 |
| Comparative Ex. 2 | $AlCl_3$ | $MgAl_{0.18}(n\text{-}C_4H_9)_{2.56}$ | 14 |
| Comparative Ex. 3 | $Al(On\text{-}C_4H_9)_2Cl$ | $MgAl_{0.41}(n\text{-}C_4H_9)_{2.43}(On\text{-}C_4H_9)_{0.80}$ | 37 |

[1] As for the composition of complex, the solution was hydrolyzed and Mg and Al were determined according to chelate titration method and $On\text{-}C_4H_9$ and $n\text{-}C_4H_9$ were determined according to gas chromatography method.

[2] The yield means that of Mg contained in the solution, based upon $Mg(n\text{-}C_4H_9)_2$.

As for the component (B) employed in Table 1, compounds other than that of the present invention are all insoluble in the solvent. Further, when $AlCl_3$ is employed as component (B) (see Comparative Example 2 mentioned below), the resulting complex contains no ($On$—$C_4H_9$) group and is different from that of the present invention.

As compared with known methods wherein an organoaluminum compound is employed as the aluminum component, firstly the aluminum component of the present invention is much stabler to air and water than said organoaluminum component, and hence is very safe for transportation, storing and handling. Further, the methods for preparing the compounds of known methods require synthesis of organoaluminum compounds or derivatives thereof, whereas the compounds of the present invention can be very easily and cheaply synthesized from an aluminum halide, metallic aluminum and an alcohol (see Referential example 1 mentioned below).

The above-mentioned second specific feature of the present invention, i.e. superiority of product, will be hereinafter described.

The complexes obtained according to the method of the present invention contain $OR^2$ or $OSiR^3R^4R^5$, and are milder in the reactivity than those containing no such groups. Accordingly, they are safe for handling, and at the same time, when they are employed as a catalyst component, it is possible to extend the range of catalyst preparation conditions, and this fact is advantageous with respect of catalyst design.

In the case of the complex of the present invention wherein Y is $OR^2$, the particle size of the resulting polymer can be made larger while maintaining the activity of the catalyst, there are no fine particles and the apparent specific gravity can be made higher, as compared with those of the prior art (see Example 35 and Comparative Examples 4 and 5 mentioned below). In the case of the complex wherein Y is $OSiR^3R^4R^5$, the groups participating in the reaction are so varied, e.g. Mg—R, Al—R and Si—H, and further, by changing the content of OSi group in addition thereto, it becomes possible to control the molecular weight and molecular weight distribution of the resulting polymer, and hence the complex is very useful. Further in the case of this complex, the reduction in activity due to the change of the amount of OSi is small, and a polymer having a sharp particle size distribution can be obtained (see Examples 36 and 37). The above-mentioned characteristic properties of catalyst are very important in the olefin polymerization process.

The method of the present invention will be further illusttrated in detail by way of the following non-limitative Examples.

EXAMPLE 1

Into a 200 ml capacity flask were introduced 0.05 mol of ethylaluminum dichloride and 50 ml of dried heptane under a nitrogen atmosphere. The contents were cooled with dry ice-methanol to −20° C., and then 50 ml of dried heptane containing 0.05 mol of n-butyl alcohol was added thereto with stirring over 30 minutes. After completion of the addition, the temperature was gradually returned to room temperature, and reaction was continued further for one hour to give a transparent solution, which was found, as the result of analysis, to be a solution of Al(On—Bu)Cl$_2$ having a concentration of 0.5 ml/l.

Then, 3.8 g (0.16 gram atom) of magnesium powder was introduced into a 500 ml capacity flask under a nitrogen atmosphere, and then thereto was added 30 ml taken from 200 ml of a dried heptane solution containing 0.15 mol of n-butylchloride. The contents of the flask were heated with stirring up to their boiling point, and after the reaction started, the remaining n-butylchloride was added over 30 minutes. After completion of the addition, heating was continued further for one hour under reflux.

To the resulting reaction mixture was added 0.014 mol of n-butoxyaluminum dichloride obtained in the above-mentioned reaction, together with 50 ml of heptane, and reaction was carried out at 80° C. for 3 hours. A solution containing magnesium in a concentration of 0.19 mol/liter was obtained. As the result of analysis, the composition of the complex thus obtained was found to be MgAl$_{0.30}$(n—C$_4$H$_9$)$_{2.60}$(On—C$_4$H$_9$)$_{0.30}$.

COMPARATIVE EXAMPLE 1

Reaction was carried out in the same manner as in Example 1, except that a heptane slurry of tri-n-butoxyaluminum was substituted for n-butoxyaluminum dichloride, to give a solution containing magnesium in a concentration of 0.09 mol/l. As the result of analysis, the composition of the complex thus obtained was

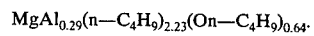

MgAl$_{0.29}$(n—C$_4$H$_9$)$_{2.23}$(On—C$_4$H$_9$)$_{0.64}$.

COMPARATIVE EXAMPLE 2

Reaction was carried out in the same manner as in Example 1, except that a heptane slurry of aluminum trichloride was substituted for n-butoxyaluminum dichloride, to give a solution containing magnesium in a concentration of 0.04 mol/l. As the result of analysis, the composition of the complex thus obtained was

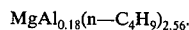

MgAl$_{0.18}$(n—C$_4$H$_9$)$_{2.56}$.

COMPARATIVE EXAMPLE 3

Reaction was carried out in the same manner as in Example 1, except that a heptane slurry of di-n-butoxyaluminum monochloride was substituted for n-butoxyaluminum dichloride, to give a solution containing magnesium in a concentration of 0.11 mol/l. As the result of analysis, the composition of the complex thus obtained was found to be

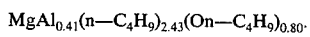

MgAl$_{0.41}$(n—C$_4$H$_9$)$_{2.43}$(On—C$_4$H$_9$)$_{0.80}$.

EXAMPLES 2-8

(A) an organomagnesium compound prepared from magnesium powder and an alkylhalide in the same manner as in Example 1, was reacted with an aluminum compound under the conditions shown in Table 2. The results are shown in Table 2.

Table 2

| Ex. No. | Magnesium compound (A) (mol) | Aluminum compound (B) (mol) | Temperature (° C) × time(hr) | Complex Concentration of Mg mol/l | Composition of complex |
|---|---|---|---|---|---|
| 2 | n-C$_4$H$_9$MgCl (0.15) | (n-C$_8$H$_{17}$O)AlCl$_2$ (0.013) | 80 × 3 | 0.20 | MgAl$_{0.17}$(n-C$_4$H$_9$)$_{2.34}$(On-C$_8$H$_{17}$)$_{0.16}$ |
| 3 | n-C$_4$H$_9$MgBr (0.15) | (isoC$_5$H$_{11}$O)AlCl$_2$ (0.014) | 80 × 3 | 0.14 | MgAl$_{0.40}$(n-C$_4$H$_9$)$_{2.81}$(Oiso-C$_5$H$_{11}$)$_{0.39}$ |
| 4 | C$_2$H$_5$MgBr (0.15) | (n-C$_4$H$_9$O)AlCl$_2$ (0.011) | 80 × 3 | 0.16 | MgAl$_{0.28}$(C$_2$H$_5$)$_{2.57}$(On-C$_4$H$_9$)$_{0.27}$ |
| 5 | n-C$_3$H$_7$MgI (0.15) | (isoC$_4$H$_9$O)AlCl$_2$ (0.025) | 80 × 3 | 0.18 | MgAl$_{0.56}$(n-C$_3$H$_7$)$_{3.11}$(OisoC$_4$H$_9$)$_{0.56}$ |
| 6 | isoC$_3$H$_7$MgCl (0.15) | (n-C$_5$H$_{11}$O)AlCl$_2$ (0.012) | 80 × 5 | 0.13 | MgAl$_{0.38}$(isoC$_3$H$_7$)$_{2.74}$(On-C$_5$H$_{11}$)$_{0.38}$ |

Table 2-continued

| Ex. No. | Magnesium compound (A) (mol) | Aluminum compound (B) (mol) | Temperature (°C) × time(hr) | Complex Concentration of Mg mol/l | Composition of complex |
|---|---|---|---|---|---|
| 7 | isoC$_4$H$_9$MgBr (0.15) | (isoC$_3$H$_7$O)AlCl$_2$ (0.010) | 90 × 3 | 0.15 | MgAl$_{0.26}$(isoC$_4$H$_9$)$_{2.51}$(OisoC$_3$H$_7$)$_{0.25}$ |
| 8 | n-C$_8$H$_{17}$MgCl (0.20) | (n-C$_5$H$_{11}$O)AlCl$_2$ (0.009) | 90 × 3 | 0.30 | MgAl$_{0.11}$(n-C$_8$H$_{17}$)$_{2.22}$(On-C$_5$H$_{11}$)$_{0.12}$ |

EXAMPLES 9–12

As shown in Table 3, (A) a dialkylmagnesium was reacted with (B) an aluminum compound, in 250 ml of heptane, at 80° C., for 3 hours. The results are shown in Table 3.

Table 3

| Ex. No. | Magnesium compound (A) (mol) | Aluminum compound (B) (mol) | Temperature (°C) × time (hr) | Complex Concentration of Mg mol/l | Composition of complex |
|---|---|---|---|---|---|
| 9 | (C$_2$H$_5$)$_2$Mg (0.10) | (isoC$_5$H$_{11}$O)AlCl$_2$ (0.016) | 90 × 4 | 0.20 | MgAl$_{0.31}$(C$_2$H$_5$)$_{2.61}$(OisoC$_5$H$_{11}$)$_{0.30}$ |
| 10 | (n-C$_4$H$_9$)$_2$Mg (0.08) | (n-C$_4$H$_9$O)AlCl$_2$ (0.013) | 80 × 3 | 0.22 | MgAl$_{0.24}$(n-C$_4$H$_9$)$_{2.48}$(OC$_4$H$_9$)$_{0.24}$ |
| 11 | (n-C$_6$H$_{13}$)$_2$Mg (0.08) | (n-C$_8$H$_{17}$O)AlCl$_2$ (0.007) | 80 × 3 | 0.19 | MgAl$_{0.15}$(n-C$_6$H$_{13}$)$_{2.31}$(O-nC$_8$H$_{17}$)$_{0.14}$ |
| 12 | (C$_6$H$_5$)$_2$Mg (0.08) | (n-C$_3$H$_7$O)AlCl$_2$ (0.025) | 80 × 3 | 0.14 | MgAl$_{0.38}$(C$_6$H$_5$)$_{2.74}$(O-nC$_3$H$_7$)$_{0.39}$ |

EXAMPLE 13

Into a 200 ml capacity flask were introduced 16 g (0.06 mol) of aluminum tribromide, 7.4 g (0.03 mol) of tri-n-butoxyaluminum and 90 ml of dried heptane under a nitrogen atmosphere. Reaction was carried out at 98° C. for 5 hours. Solid components completely dissolved to give a transparent solution, which was found, as the result of analysis, to be a solution of Al(On—Bu)Br$_2$ in a concentration of 1 M/l.

Then, 7.6 g (0.32 gram atom) of magnesium powder was introduced into a 500 ml capacity flask under a nitrogen atmosphere, and then thereto was added 30 ml taken from 200 ml of a dried heptane solution containing 0.30 mol of n-butylchloride. The contents of the flask were heated with stirring up to their boiling point. Since the reaction started, the remaining n-butylchloride was added over 30 minutes. After completion of the addition, heating was carried out for another one hour under reflux.

To the resulting reaction mixture were added 0.010 mol of n-butoxyaluminum dibromide obtained in the above-mentioned reaction, together with 50 ml of heptane. Reaction was carried out at 80° C. for 3 hours to give a solution containing magnesium in a concentration of 0.35 mol/l. As the result of analysis, the composition of the complex thus obtained was found to be

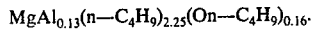

EXAMPLES 14–22

(A) an organomagnesium compound prepared from magnesium powder and an alkylhalide in the same manner as in Example 1, was reacted with (B) an aluminum compound under the conditions shown in Table 4. The results are shown in Table 4.

Table 4

| Ex. No. | Magnesium compound (A) (mol) | Aluminum compound (B) (mol) | Temperature (°C) × time(hr) | Complex Concentration of Mg mol/l | Composition of complex |
|---|---|---|---|---|---|
| 14 | n-C$_4$H$_9$MgCl (0.15) | (n-C$_8$H$_{17}$O)AlBr$_2$ (0.008) | 98 × 3 | 0.17 | MgAl$_{0.17}$(n-C$_4$H$_9$)$_{2.34}$(O n-C$_8$H$_{17}$)$_{0.16}$ |
| 15 | n-C$_3$H$_7$MgBr (0.20) | (n-C$_3$H$_7$O)AlI$_2$ (0.016) | 98 × 2 | 0.23 | MgAl$_{0.38}$(n-C$_3$H$_7$)$_{2.75}$(O n-C$_3$H$_7$)$_{0.39}$ |
| 16 | n-C$_5$H$_{11}$MgBr (0.40) | (n-C$_4$H$_9$O)AlI$_2$ (0.021) | 60 × 5 | 0.45 | MgAl$_{0.19}$(n-C$_5$H$_{11}$)$_{2.36}$(O n-C$_4$H$_9$)$_{0.19}$ |
| 17 | n-C$_4$H$_9$MgBr (0.45) | (iso-C$_3$H$_7$O)AlI$_2$ (0.075) | 60 × 5 | 0.60 | MgAl$_{0.49}$(n-C$_4$H$_9$)$_{2.99}$(OisoC$_3$H$_7$)$_{0.48}$ |
| 18 | n-C$_6$H$_{13}$MgCl 0.30 | (n-C$_5$H$_{11}$O)AlBr$_2$ (0.024) | 60 × 8 | 0.38 | MgAl$_{0.26}$(n-C$_6$H$_{13}$)$_{2.54}$(O n-C$_5$H$_{11}$)$_{0.23}$ |
| 19 | n-C$_8$H$_{17}$MgCl 0.30 | (iso-C$_3$H$_7$O)AlBr$_2$ (0.037) | 98 × 1 | 0.42 | MgAl$_{0.35}$(n-C$_8$H$_{17}$)$_{2.72}$(OisoC$_3$H$_7$)$_{0.35}$ |
| 20 | C$_2$H$_5$MgCl 0.15 | (isoC$_4$H$_9$O)AlBr$_2$ (0.005) | 98 × 3 | 0.11 | MgAl$_{0.12}$(C$_2$H$_5$)$_{2.21}$(OisoC$_4$H$_9$)$_{0.14}$ |
| 21 | iso-C$_3$H$_7$MgI (0.40) | (n-C$_8$H$_{17}$O)AlI$_2$ (0.037) | 98 × 3 | 0.34 | MgAl$_{0.43}$(iso-C$_3$H$_7$)$_{2.87}$(O n-C$_8$H$_{17}$)$_{0.42}$ |
| 22 | iso-C$_4$H$_9$MgI (0.40) | (C$_6$H$_5$O)AlBr$_2$ (0.024) | 98 × 8 | 0.26 | MgAl$_{0.37}$(iso-C$_4$H$_9$)$_{2.74}$(OC$_6$H$_5$)$_{0.36}$ |

EXAMPLE 23

Into a 200 ml flask were introduced 0.05 mol of ethylaluminum dichloride and 50 ml of dried heptane, under a nitrogen atmosphere, and then was added 50 ml of a dried heptane solution containing 0.05 mol of polyhydromethylsiloxane. Reaction was carried out under reflux by heating for 3 hours. The resulting reaction solution was found, as the result of analysis, to be a 250 ml of heptane under the conditions shown in Table 6. The results are shown in Table 6.

Table 6

| Ex. No. | Magnesium compound (mol) | Aluminum compound (mol) | Temperature (° C) × time(hr) | Complex Concentration of Mg (mol/l) | Composition of complex |
|---|---|---|---|---|---|
| 32 | $(n-C_4H_9)_2Mg$ (0.08) | $(H . C_2H_5 . C_6H_5SiO)AlCl_2$ (0.013) | 80 × 1 | 0.19 | $MgAl_{0.28}(n-C_4H_9)_{2.55}(OSiH . C_2H_5 . C_6H_5)_{0.27}$ |
| 33 | $(C_2H_5)_2Mg$ (0.08) | $(H . C_2H_5 . n-C_4H_9SiO)AlBr_2$ (0.014) | 98 × 4 | 0.17 | $MgAl_{0.34}(C_2H_5)_{2.68}(OSiH C_2H_5 . n-C_4H_9)_{0.36}$ |
| 34 | $(n-C_6H_{13})_2Mg$ (0.15) | $[H . C_2H_5 . C_6H_5SiO]AlCl_2$ (0.026) | 98 × 10 | 0.43 | $MgAl_{0.24}(n-C_6H_{13})_{2.45}[OSiH . C_2H_5 . C_6H_5]_{0.26}$ | solution of $(H.CH_3.C_2H_5 SiO)AlCl_2$ having a concentration of 0.5 mol/l.

Then, 3.8 g (0.16 gram atom) of magnesium powder was introduced into a 500 ml flask under a nitrogen atmosphere and then thereto was added 30 ml taken from 200 ml of a dried heptane solution containing 0.15 mol of n-butylchloride. Stirring was carried out under reflux by heating. Once the reaction started, the remaining solution of n-butylchloride was added over 30 minutes. After completion of the addition, heating was continued further for one hour under reflux.

To the resulting reaction mixture were added 0.009 mol of $(H.CH_3.C_2H_5 SiO)AlCl_2$ obtained in the above-mentioned reaction, together with 50 ml of heptane. Reaction was carried out at 98° C. for 3 hours to give a solution containing magnesium in a concentration of 0.13 mol/l. As the result of analysis, the composition of the complex thus obtained was found to be

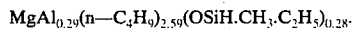

$MgAl_{0.29}(n-C_4H_9)_{2.59}(OSiH.CH_3.C_2H_5)_{0.28}$.

EXAMPLES 24–31

Various kinds of magnesium compounds and aluminum compounds prepared in the same manner as in Example 23 were reacted together in 250 ml of heptane under the conditions shown in Table 5. The results are shown in Table 5.

EXAMPLES 35-37 AND COMPARATIVE EXAMPLES 4 and 5

In these Examples and Comparative Examples, catalyst preparation and polymerization were carried out in order to show the usefulness of the complexes of the present invention for an ethylene polymerization catalyst.

(1) Preparation of solid catalyst 1.2 l of dried hexane was introduced into a 4 l capacity reactor equipped with a stirrer the inside of which reactor had been dried in vacuo and purged with nitrogen, and the hexane was kept at 0° C. with stirring. Two dropping funnels were connected to this reactor. 600 ml of a hexane solution of titanium tetrachloride in a connection of 1.0 mol/l was introduced into one of the funnels and 600 ml of a complex solution (adjusted to a concentration of 1.0 mol/l in hexane) shown in Table 7 was introduced into the other funnel. The two components were dropped from the funnels, with stirring at 0° C. over 3 hours. Further, stirring was continued at this temperature for one hour to effect reaction. The resulting solid component was isolated and dried.

(2) Polymerization 800 ml of heptane was introduced into a 1.5 l capacity autoclave the inside of which had been purged with nitrogen. While maintaining the temperature at 85° C., Table 5

| Ex. No. | Magnesium compound (mol) | Aluminum compound (mol) | Temperature (° C) × time(hr) | Complex Concentration of Mg (mol/l) | Composition of complex |
|---|---|---|---|---|---|
| 24 | $n-C_8H_{17}MgCl$ (0.15) | $(H . CH_3 . C_2H_5SiO)AlCl_2$ (0.009) | 80 × 3 | 0.21 | $MgAl_{0.17}(n-C_8H_{17})_{2.32}(OSi . H . CH_3 . C_2H_5)_{0.17}$ |
| 25 | $n-C_{10}H_{21}MgCl$ (0.15) | $(H . CH_3 . n-C_4H_9SiO)AlBr_2$ (0.020) | 98 × 2 | 0.22 | $MgAl_{0.18}(n-C_{10}H_{21})_{2.34}(OSiH . CH_3 . n-C_4H_9)_{0.18}$ |
| 26 | $n-C_3H_7MgCl$ (0.15) | $(H . CH_3 . C_6H_5SiO)AlI_2$ (0.013) | 98 × 3 | 0.15 | $MgAl_{0.37}(n-C_3H_7)_{2.74}(OSiH . CH_3 . C_6H_5)_{0.36}$ |
| 27 | $n-C_4H_9MgCl$ (0.15) | $[(CH_3)_2 . n-C_4H_9SiO]AlCl_2$ (0.012) | 98 × 3 | 0.16 | $MgAl_{0.30}(n-C_4H_9)_{2.61}[OSi(CH_3)_2 . n-C_4H_9]_{0.30}$ |
| 28 | $n-C_4H_9MgCl$ (0.23) | $(H_2CH_3SiO)AlCl_2$ (0.021) | 70 × 5 | 0.44 | $MgAl_{0.19}(n-C_4H_9)_{2.36}(OSiH_2 . CH_3)_{0.20}$ |
| 29 | $iso-C_4H_9MgCl$ (0.25) | $[H . (CH_3)_2SiO]AlCl_2$ (0.018) | 98 × 10 | 0.20 | $MgAl_{0.39}(iso-C_4H_9)_{2.78}[Osi(CH_3)_2H]_{0.38}$ |
| 30 | $n-C_4H_9MgBr$ (0.15) | $(H . CH_3 . iso-C_4H_9SiO)AlCl_2$ (0.020) | 98 × 6 | 0.14 | $MgAl_{0.58}(n-C_4H_9)_{3.15}(OSiH . CH_3 . iso-C_4H_9)_{0.57}$ |
| 31 | $C_2H_5MgI$ (0.15) | $[H . (C_2H_5)_2SiO]AlCl_2$ (0.018) | 98 × 5 | 0.15 | $MgAl_{0.47}(C_2H_5)_{2.95}[OSiH . (C_2H_5)_2]_{0.48}$ |

EXAMPLES 32–34

Various kinds of dialkylmagnesiums and aluminum compounds shown in Table 6 were reacted together in 2.0 Kg/cm² of hydrogen and 2.0 Kg/cm² of ethylene were pressurized into the autoclave to raise the total pressure to 4.0 Kg/cm². Ten mg of the solid component obtained in step (1) and 0.4 mmol of triisobutylaluminum were added to the autoclave. Polymerization was carried out for 30 minutes, while supplying ethylene. The results are shown in Table 7.

Table 7

| Ex. | Preparation method | Complex Composition | Yield (g) | Bulk Density (g/cc) | Particle size distribution of polymer particles mesh % |  |  |  |  |  |  |
|---|---|---|---|---|---|---|---|---|---|---|---|
| | | | | | <20 | 20-35 | 35-48 | 48-100 | 100-145 | 145-200 | >200 |
| 35 | Al(On-C₄H₉)Cl₂ of Example 1 was used. | MgAl₀.₂₂(n-C₄H₉)₂.₄₄(On-C₄H₉)₀.₂₅ | 215 | 0.41 | 0 | 13 | 45 | 28 | 14 | 0 | 0 |
| 36 | (H.CH₃.C₆H₅SiO)-AlCl₂ of Example 23 was used | MgAl₀.₃₂(n-C₄H₉)₂.₆₆(OSi.H.CH₃.C₆H₅)₀.₃₃ | 198 | 0.37 | 0 | 0 | 5 | 12 | 75 | 8 | 0 |
| 37 | " | MgAl₀.₇₂(n-C₄H₉)₃.₃₁(OSi.H.CH₃.C₂H₅)₀.₈₅ | 182 | 0.39 | 0 | 0 | 6 | 19 | 69 | 6 | 0 |
| Comparative Ex. 4 | Al(On-C₄H₉)₃ of Comparative Ex. 1 was used. | MgAl₀.₃₂(n-C₄H₉)₂.₀₆(On-C₄H₉)₀.₁₈₅ | 142 | 0.28 | 5 | 9 | 16 | 22 | 25 | 13 | 10 |
| Comparative Ex. 5 | AlCl₃ of Comparative Ex. 2 was used. | MgAl₀.₁₀(n-C₄H₉)₂.₅₅ | 165 | 0.30 | 18 | 5 | 7 | 17 | 20 | 15 | 18 |

REFERENTIAL EXAMPLE 1

Into a 200 ml capacity flask were introduced 8.0 g (0.06 mol) of aluminum trichloride, 0.81 g (0.03 mol) of aluminum powder and 2.2 g (0.030 mol) of n-butanol, together with 90 ml of dried hexane, under a nitrogen atmosphere. A reflux condenser was attached to the flask, and reaction was carried out for 2 hours at the reflux temperature of the contents. Aluminum trichloride and aluminum powder both of which were initially insoluble, reacted to give a uniform solution. This solution was found, as the result of analysis, to be a solution of Al(On—C₄H₉)Cl₂ having a concentration of 1.1 mol/l.

It will be appreciated that the instant specification and claims are set forth by way of illustration and not limitation, and that various modifications and changes may be made without departing from the spirit and scope of the present invention.

What is claimed is:

1. A method for producing a hydrocarbon-soluble organomagnesium complex of the formula $$Mg_\alpha Al_\beta R^1_p Y_q$$

wherein
$\alpha$, $\beta$, $p$ and $q$ each is a number greater than zero,
$\alpha/\beta$ = about 0.5 to 20,
$2\alpha$ and $3\beta = p + q$,
$q/\beta$ = about 0.5 to 1.5,
$Y$ is $OR^2$ or $OSiR^3R^4R^5$,
$R^1$, $R^2$ and $R^3$ each independently is a hydrocarbon radical having 1 to 20 carbon atoms, and
$R^4$ and $R^5$ each independently is a hydrocarbon radical having 1 to 20 carbon atoms, hydrogen or a halogen atom, which comprises reacting in an inert hydrocarbon medium at a temperature of about 50°-150° C. and for about 0.5 to 20 hours
(A) an ether-free solution containing about 0.1-2.5 mols per liter of organomagnesium compound of the formula $$R^1_a MgX_{2-a}$$

with (B) a solution containing about 0.005-5 mols per liter of an aluminum compound of the formula $$AlYX_2$$

wherein
X is a halogen atom, and
$a$ is a positive number up to 2.
2. The method according to claim 1,
wherein
$\alpha/\beta$ = about 1 to 10,
at least one of $R^4$ and $R^5$ is hydrogen, and X is chlorine.
3. The method according to claim 1 wherein $R^1$ is an aliphatic hydrocarbon group.
4. The method according to claim 1 wherein Y is $OR^2$.
5. The method according to claim 3 wherein Y is $OR^2$.
6. The method according to claim 4 wherein $R^2$ is propyl, butyl or amyl.
7. The method according to claim 1 wherein Y is $OSiR^3R^4R^5$.
8. The method according to claim 7 wherein at least one of $R^4$ and $R^5$ is a hydrogen atom.
9. The method according to claim 3 wherein Y is $OSiR^3R^4R^5$.
10. The method according to claim 9 wherein at least one of $R^4$ and $R^5$ is a hydrogen atom.

* * * * *